(12) United States Patent
Morseman et al.

(10) Patent No.: US 6,809,186 B1
(45) Date of Patent: Oct. 26, 2004

(54) SIMPLE METHOD FOR LABELED CONJUGATE PRODUCTION

(75) Inventors: John P. Morseman, Columbia, MD (US); Xiangfei Zeng, Beaverton, OR (US)

(73) Assignee: Martek Biosciences Corporation, Columbia, MD (US)

( * ) Notice: Subject to any disclaimer, the term of this patent is extended or adjusted under 35 U.S.C. 154(b) by 0 days.

(21) Appl. No.: 09/889,795

(22) PCT Filed: Jan. 22, 2000

(86) PCT No.: PCT/US00/01350

§ 371 (c)(1),
(2), (4) Date: Dec. 6, 2001

(87) PCT Pub. No.: WO00/43784

PCT Pub. Date: Jul. 27, 2000

Related U.S. Application Data

(60) Provisional application No. 60/116,689, filed on Jan. 22, 1999.

(51) Int. Cl.[7] .............................. C07K 1/04; C07K 1/13; C12N 9/96; C12N 11/06; C12N 11/12
(52) U.S. Cl. .............................. 530/409; 435/6; 435/7.5; 435/188; 436/527; 436/529; 436/530; 436/533; 530/402; 530/408; 530/811; 530/814; 530/816
(58) Field of Search ........................ 435/188.6, 7.5, 435/188; 436/527, 529, 530, 533, 526; 530/402, 408, 409, 811, 814, 816

(56) References Cited

U.S. PATENT DOCUMENTS

2003/0035786 A1 * 2/2003 Hendriks et al.

FOREIGN PATENT DOCUMENTS

WO    WO9727885    8/1997

OTHER PUBLICATIONS

Dagenais, P., et al., "Direct Covalent Attachment Of Small Peptide Antigens To Enzyme–Linked Immunosorbent Assay Plates Using Radiation And Carbodiimide Activation", Analytical Biochemistry; vol. 222, No. 1, p. 149–155 (1994).

Lewis, M. R., et al., "A Facile Water–Soluble Method For Modification Of Proteins With DOTA", Bioconjugate Chemistry, vol. 5, No. 6, p. 565–576 (1994).

Ghosh, M. K., et al., "Preparation And Characterization Of Methotrexate–Immunoglobulin Conjugates", Drug Design and Delivery, vol. 4, No. p. 13–25 (1989).

Han, Z., et al., "Covalent Coupling Of Papain And N–Hydroxysuccinimide Esters Of Crosslinked Agarose", Chemical Abstracts, vol. 113, No. 21, p. 325, Abstr. No. 187238 (1990).

* cited by examiner

Primary Examiner—Mary E. Ceperley
(74) Attorney, Agent, or Firm—Hunton & Williams LLP

(57) ABSTRACT

The present invention relates to methods for coupling labels to particular target moieties. The coupling reactions of the present invention use temporal spacing of the reactants through phase change (i.e. by rapid freezing) to control the initiation and termination of reaction. This process results in a simplified and improved method for linking labels to specific binding moieties using N-hydroxysuccinimide chemistry. The present invention further relates to kits comprising all necessary components to easily and rapidly make protein conjugates.

5 Claims, 2 Drawing Sheets

SIMPLE METHOD FOR LABELED CONJUGATE PRODUCTION

THIS APPLICATION IS A 371 OF PCT/US00/01350 Jan. 22, 2000 and claims benefit of 60/116,689 Jan. 22, 1999.

BACKGROUND OF THE INVENTION

1. Field of the Invention

This invention relates to the attachment of detectable labels to molecules containing free amino groups (e.g., proteins, nucleic acids and amino sugars), the molecules having specific binding sites thereby providing a method of directing the label to the moiety specifically bound by the labeled molecule.

2. Review or Related Art

N-hydroxysulfosuccinimide (NHS) esters provide one of the most common activation chemistries for creating reactive acylating agents. Homobifunctional NHS esters were first introduced as reactive cross-linking agents in the early 1970's and are widely available commercially. [Bragg, P., & Hou, C. (1975), "Subunit composition, function and spatial arrangement on the $Ca^{2+}$ and $Mg^{2+}$ activated adenosine triphosphatases of *Escherichia coli* and *Salmonella typhimurium*," *Eur. J Biochem.*, 106, 495–503, Lomant, A. & Fairbanks, G. (1976)*J. Mol. Biol.*,104, 243–261.] NHS esters are routinely used to conjugate proteins to each other via heterobifunctional cross-linking agents (e.g. see all of Pierce Chemicals "Double Agents" that have an NHS side; Muramoa K, Kamiya H (1988) "Preparation and characterization of a cleavable photoactiviable heterobifunctional fluoresent reagent for proteins." *Agric. Biol Chem.* 52, 547–554) or to dyes (such as acridinium; Zomer G., Van den Berg R.H., Jansen E.H.J.M. (1988) "Optimal labelling of proteins with acridinium ester" *Anal. Chim. Acia*, 205, 267–271.

N-hydroxysuccinimide (NHS) chemistry

A NHS ester is formed by the reaction of a carboxylate with NHS in the presence of a carbodiimide. To prepare a stable ester, the reaction must be done in non-aqueous environments, otherwise it will degrade with non-productive reactions; aqueously prepared esters are unstable and breakdown in a matter of hours under the best of conditions. The NHS ester- or sulf-NHS ester-containing reactant reacts with a nucleophile to form an acylated product with the release of NHS or sulfo-NHS leaving group. The reaction is non-productive with imidazolyl ring nitrogens, sulfhydral or hydroxyl groups, forming aqueously degraded ester or thioester bonds. Reactions with primary and secondary amines create stable amide and imide linkages, respectively.

In proteins these reagents principally react with alpha amines at the N-terminals and the epsilon amines of lysine side chains. It is possible to create NHS esters in situ to react immediately with target molecules in aqueous media (Staros, i., Wright, R. & Swingel, D. (1986),*Anal. Biochem.*, 156, 220–222; Staros, J. (1982), *Biochemistry* 21, 3950–3955). NHS esters have a half-life in aqueous environments at pH 7 on the order of several hours (4–5 hours at 0° C. pH 7.0, Lomant, A. & Fairbanks, G. (1976), *J Mol. Biol.*, 104, 243-261).

Carbodiimides are zero length cross-linkers that mediate the formation of an amide or phosphoramidate linkage between a carboxylate and an amine, or a phosphate and an amine, respectively. (Chu, B., Kramer, F. & Orgel, L. (1986), "Synthesis of an amplifiable reporter RNA for bioassays," *Nucleic Acids Research*, 14, 5591–5603. Hoare, D. & Koshland, D.E. (1966) *J. Am. Chem. Soc.,* 88, 2057.) They react with carboxylic acids to form highly reactive O-acylisourea compounds that are very short lived but react with nucleophiles to form an amide bond. There are several competing and non-productive reactions, such as with water to regenerate the carboxylate group. This reaction works effectively between pH 4.5 and 7.5. Molecules with a phosphate group such as the 5' phosphate on oligonucleotides can also react with amine-containing groups by using the carbodiimide reaction.

DCCD (a carbodiimide) and NHS have been used to activate a microplate surface, which was then washed and protein added to the well to facilitate covalent attachment of the protein to the plate. (Dagenais P., Desprez B., Altert J., Escher E. (1994), *Anal. Biochem.*, 222, 149–155)

A method for use of EDAC (a carbodiimide) and sulfo-NHS is summarized in Hermanson, G.T., *Bioconjugate Techniques*, Academic Press, New York, London, 1966.

A protein/label complex has been made into a NHS derivative such that when it bonded to the protein transporter it would complex there and allow visualization of the position of the transporter. This is basically an activated protein/dye complex that has an active NHS on it. (Fan J., Pope L.E., Vitols K.S., Huennekens F.M. (1991), "Affinity labeling of folate transport protein with the N-hydroxysuccinimide ester of the g isomer of fluoreseinmethotrexate." *Biochem.*, 30, 4573–4580]. NHS activated dyes are also sold on a commercial basis (e.g., see the activated Cyanine dyes sold by Amersham Pharmacia Biotech, such as FluoroLink™Cy5™ or Flurolink™Cy5.5™).

A NHS ester of 4-hydroxytestosterone-4-hemiglutarate has been made by treatment with carbodiimide and NHS. This was mixed with horse-radish peroxidase (HRP) or β-galactosidase to make a 4HT-4-HG that was enzyme labeled. The enzyme labeled hydroxytestosterone was used for tracer studies (Hosada H., Karube T., Kobayashi N., Nambara T. (1985), "Enzyme labeling of steroids by the N-succinimidyl ester method. Preparation of horse-radish peroxidase-labelled antigen for use in enzyme immunoassay." *Chem. Pharm. Bull.*, 33, 249–255).

SUMMARY OF THE INVENTION

The present invention is directed to simplified methods for coupling labels to particular target moieties. Such coupling is usually accomplished by activating the label, the target moiety, or both with highly reactive activating chemicals. The usual coupling protocols are problematic because the activating chemicals are prone to uncontrolled reactions which produce unwanted side-products, or a too rapid reaction resulting in dissipation of the activating chemicals without the desired coupling. Coupling reactions according to the present invention use temporal spacing of the reactants through phase change (e.g., by rapid freezing) to control the initiation and termination of reaction instead of physical spacing of the traditional method.

For example, the technique of generating NHS esters in situ (with no freeze-drying, just adding in reagents) is mentioned in *Bioconjugate Techniques*. This invention uses the same chemistry and the same idea of getting a label bound to another molecule, but the difference is the easy-to-use format (i.e., the "one tube format"). In this method, all reactants are prepared separately then combined in such a way that they do not react with each other until the targeted compound is added to activate the cross-linking chemicals. One such format is done by sequentially flash freezing aqueous solutions of the reactants then freeze-drying them together as a unit (e.g., in a microcentrifuge tube). In another format of this invention, freeze-dried or otherwise dried components are prepared separately and then combined in a dry form or in a spatially separate format (e.g., in the top of a microcentrifuge tube that is sectioned into separate parts), such that the water soluble components are not in condition to react with each other until addition of the compound to be labeled (in aqueous form).

This invention provides an improved method of linking labels to specific binding moieties (e.g., moieties that are useful for selecting analytical targets) using N-hydroxysuccinimide (NHS) chemistry. In particular, the invention provides for the separation and stabilization of the active components achieved through sequential or separate freezing in the appropriate buffers (essentially spatial or temporal separation of components prior to utilization).

In another mode, this invention provides a kit comprising NHS, a water soluble carbodiimide (e.g., EDAC) and a label containing an amine or carboxyl moiety, these components being in dry form suitable for rehydration at a pH around 7 in which all components have sufficient activity for activation and cross-linkage.

While phycobiliproteins have been considered complicated to conjugate, this invention provides a method for rapidly and easily making stable phycobiliprotein conjugates to specific target binding proteins. SMCC and SPDP pre-activated phycobiliproteins have been available in several formulations. However, this invention provides a simpler method for making conjugates in that it requires fewer steps and is more rapid. In fact, this invention allows a researcher to easily label whatever specific binding molecule they would like with a carboxyl-containing label (e.g., phycobiliprotein, enzyme, PBXL™, etc.) This invention provides for kits to make a conjugate, so that the person using the kit does not have to be an expert at protein conjugation to obtain useable conjugates at the end of the process.

DETAILED DESCRIPTION OF THE INVENTION

Figure 1:
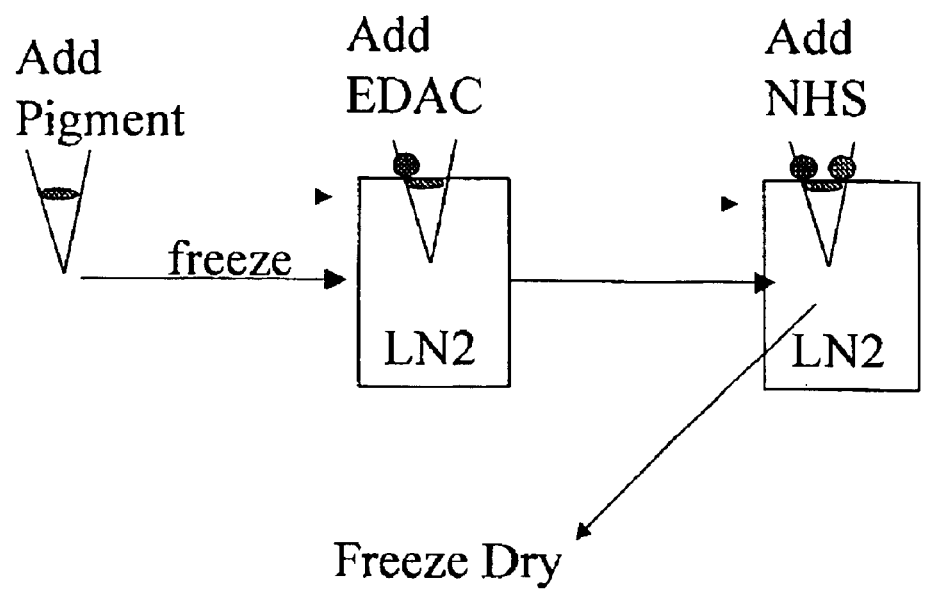
FIG. 1 a schematic representation showing the steps involved in one embodiment of the method of this invention.

The method of this invention allows a person to add a target moiety to be labeled (e.g., a protein provided in a buffered solution) to a dry powder containing a detectable label (such as a phycobiliprotein, enzyme, protein or PBXL™ phycobilisome dye), buffer, NHS and carbodiimide, such that, once the dry powder is hydrated, a reactive NHS ester is created that links the detectable label to the target protein in a single step. The labeled targeting moiety can either be used directly as a tracer (before or after quenching) or further purified to remove unbound dye and quenching reagent, thus providing a highly purified labeled compound.

In one embodiment, the invention provides a kit including a reaction vessel (e.g., a microcentrifuge tube) containing freeze-dried EDAC (the carbodiimide), a labeling moiety (e.g., phycobiliprotein, phycobilisome or other), and NHS. These components are not yet reacted with each other, but were added and frozen in a sequential fashion in their own optimal buffers to maintain the stability of each component (since EDAC and NHS are stable at different pHs). On rehydration at a pH straddling the optima of these reagents, an environment conducive to completing the reaction is created to make useable conjugate (even though the environment is not optimal for either the carbodiimide or the NHS).

This same format can be used for other types of cross-linking agents that require the target molecules to be first modified prior to use, if suitable reaction conditions, including proper pH ranges, are utilized for the particular chemistries being applied. For example, simple cross-linking of a protein of interest to a label may be accomplished with the use of SMCC (succinimidyl 4-(N-maleimidomethyl) cyclohexane-1-carboxylate) or any of its derivatives and reductants such as dithiothreitol (DTT) or β-mercaptoethanol. These chemicals are frozen sequentially then freeze-dried. The freeze-dried materials are then rehydrated with the protein to be conjugated dissolved in buffer. This activates the materials and, upon removal of the reductant through desalting or dialysis, allows them to be cross-linked to each other. Careful coordination of the protein ratios is necessary for optimal conjugates. Sequential additions of buffer and target compound could improve the resulting product. This embodiment of the present invention also includes a kit where materials (protein, oligonucleotide probes etc.) are sequentially frozen within a matrix to which the desired attachment partner (target moiety) is added and subsequently reduced while allowing the reductant to be slowly removed, thereby driving the conjugation reaction and resulting in defined conjugates of desired and specific molar ratios. Such a matrix could be as simple as a high molecular weight dialysis tubing containing the reductant and the activated protein, or as complex as a reaction vessel that allows for slow spatial separation of reductants through gel filtration (i.e., desalting) or chemical/thermal inactivation.

Advantages of this method are that it is simple and provides a way for a researcher who may be skeptical of doing his or her own conjugation to have rapid success. Carried to its logical conclusion, it is possible to balance the ratios such that little or no quench would be needed and one can mix, incubate, then use the label directly. Alternatively, the reacted conjugate may be purified over a gel permeation column or other type of separation step to obtain highly purified conjugate.

Summary of Experimental Work

The present invention was developed from experimental work carried out in an effort to find a stable NHS ester or other functional reactive cross-linking agent for attachment of proteins, specifically labels, to other proteins and nucleic acids, with the goal of making it as user friendly as possible. In particular it was desired to provide an easy, one-step method for the conjugation of two proteins. Several experimental approaches were undertaken.

First, liquid NHS ester conjugates were made between streptavidin (SA) and various detectable labels, allophycocyanin (APC), stabilized phycobilisomes (PBXL-3), or phycoerythrin (PE), to determine the suitable conditions and ratios for adequate coupling. Since the NHS ester has a relatively short half life in near neutral conditions due to hydrolysis of the ester, the long term stability of the active NHS ester cross-linked to protein was found to be not conducive to a product that might need a shelf life of at least 6 months.

The next approach was to make the same active NHS ester protein complex using basically the same protocol with the addition of trehalose to enhance the stability of the phycobiliprotein to freezing and then immersing the whole complex in liquid nitrogen until thoroughly frozen, followed by freeze-drying of the whole complex. The freeze-dried complex was then resuspended in a streptavidin solution, and the resulting conjugate was compared against the conjugate made in a liquid format. The results clearly show a substantial loss in absolute binding capacity by the freeze-dried complex. The freeze-dried active NHS ester protein complex never out-performed the liquid complex.

As an alternative to trying to maintain a stable complex for long periods of time, the inventors investigated a protocol in which the complex was not formed until they were ready to couple the detectable label and SA together. Materials were added sequentially and frozen at each addition, first the label, then the EDAC and finally the sulfo-NHS. However, the order of this addition is of little consequence since the reagents are separated by freezing. Almost instantaneous freezing of the layers and extremely cold temperature essentially rendered the materials inert with respect to each other. The frozen compositions were then freeze-dried. Conjugates were formed when aqueous protein solutions were added to the freeze-dried powder. The resulting conjugates act very similarly to their liquid-formed counterparts, with the ability to generate similar signal when run on a BSA-Biotin microplate assay.

Producing NHS activated pigments

The invention provides these benefits by putting the three ingredients (labeling moiety, NHS, and carbodiimide) together without reacting with each other until desired. Typically this is accomplished by a sequential addition of reagents and rapid freezing, followed by a freeze-drying step, such as that shown in FIG. 1. This could also be achieved by freeze-drying (or otherwise drying) each component separately and making each into homogeneous powders that could be mixed in the proper ratios as a bulk reagent under moisture-free conditions Types of labels—

Suitable labels are detectable moieties that have free carboxyl groups. Preferably the label moiety does not have free amines, but the concentration of label must be adjusted to minimize label-to-label cross-linking in all cases (with or without amines). In order to prevent possible inter-pigment bridging, acylating reagents such as acetic anhydride may be used to convert amines to carboxyl groups (in the case of acetic anhydride) or other groups non-reactive with the NHS such as thiols (e.g., SATA). The label must have some property that allows it to be monitored once coupled to one half of a specific binding pair. This could be fluorescence, chromgenicity, radioactivity, enzyme activity, physical density, etc. For convenience, activated labels may be referred to as "pigments," but any detectable moiety that can be coupled via NHS chemistry may be used, regardless of light absorption. Typical labels include, but are not limited to, those listed below:

phycobiliproteins (e.g., allophycocyanin, phycocyanin, phycoerythrin, phycoerythrocyanin, CryptoFluor™ dyes), subunits of the phycobiliproteins (e.g., alpha, beta and gamma subunits of phycoerythrin), phycobilisomes (cyanobacterial or red algal), including phycobilisome subcomplexes a (rods and core), stabilized phycobilisomes, including stabilized phycobilisome subcomplexes (rods and core) or chemically stabilized phycobilisomes, such as those isolated from *Porphyridium cruentum* or *Arthrospira platensis* (e.g., PBXL-1 or PBXL3, respectively), or tandem dyes containing these chemically stabilized phycobilisomes and Cy 5.5 (e.g., PBXL-2 or PBXL-4, respectively), enzymes (horse-radish peroxidase, alkaline phosphatase, DNA polymerase, RNA polymerase), latex beads (e.g., natural, dyed, activated), nucleic acids (e.g., RNA, DNA, PNA), modified nucleic acids (e.g., methylated, biotinylated, amine terminated), agarose beads (e.g., Sepharose™, Sephadex™), activated glass beads (e.g., modified CPG beads), magnetic beads (e.g., BioMag™), Lanthanide containing chelates, such as cryptates (e.g., europium, terbium), modified to contain free carboxyl groups or free amines, Organic dyes with free amine—such as amine containing aminofluorescein derivatives (e.g. fluorescein-5-thiosemicarbazole, 5-(((2-(Carbohyazino)methyl)thio)acetyl)-aminofluorescein, aminofluorescein) or rhodamine.

recombinant or native protein fluors, such as Green Fluorescent Protein, Red Fluorescent Protein, Blue Fluorescent Protein and Yellow Fluorescent Protein.

Types of NHS—
N-hydroxysuccinimide
Sulfo-N-hydroxysuccinimde
Water soluble NHS analogs
Types of water soluble carbodiimides—
[EDAC] I-ethyl-33-dimethylaminopropyl)-carbodiimide
[CMC] I-cyclohexyl-3-(2-morpholino4-ethyl)-carbodiimide
[DCC] dicyclohexyl carbodiimide
[DIC] diisopropyl carbodiimide
Other possible cross-linking agents—
[Woodward's Reagent K] N-ethyl-3-phenylisoxaxoliurn-3'-sulfonate
[CDI] N,N'-carbonyidiimidazole
Methods of preparing reactive powder—

The reagents are dried in a sequential manner to separate the reactants from each other while maintaining the proper environment (e.g., pH) that maintains the compounds in the best form possible. For example, the label is added in aqueous form, frozen in liquid nitrogen, then the NHS is put in on top of this and instantly frozen, then the EDAC is added and instantly frozen. This entire construct is freeze-dried and the resulting tube stored under desiccation until needed. Alternative procedures for preparing the powder containing the label and other necessary reactants include:

Freeze-drying/temporal separation of phases—The liquids are added and frozen sequentially, thereby separating the different pHs and reagents as frozen parts that do not mix. Then the whole thing is freeze-dried. (actual)

Reagent stock solutions are frozen independently, freeze-dried and then reduced to a fine powder in a moisture-free environment. This is then added either separately to tubes or combined in proper proportion with the other reagents prior to dispensing into tubes for use.

Dry chemicals are dispensed into tubes as single components, rather than being freeze-dried sequentially. They would then be mixed on addition of water to start the activation of the label. After a suitable incubation period, the compound (amine containing) would be added to react with the carbodiimide activated carboxyl. The resultant material is then dispensed in the proper weights to the reaction tubes.

Dry chemicals are mixed to make the buffer then dispensed to the reaction chamber. Dry NHS and carbodiimide are added to the reaction mixture in proper proportion. All are sealed in a moisture free environment, preferably under vacuum until use. (prophetic)

The order of additions is not relevant to the outcome using the above protocol. It is important to make sure that the materials are rapidly frozen and do not significantly thaw the preceding layer. This can be accomplished by maintaining very cold (liquid nitrogen or dry ice) temperatures for the tube getting the liquid and using very cold solutions for the additions. It is most simple to add materials with the largest volumes first, then add the smaller volumes. The sides of the tubes can be used for implementing freezing prior to having the layers meet.

The materials could be pre-blended as freeze-dried or flash dried powders instead of layering as described above. In this case it will be harder to make the smaller tubes because such small amounts of material will be added to each tube. However, once blended, an automated dispenser could weigh materials into tubes in a very defined manner.

Kit Form

In a preferred mode, the reactive powder containing a detectable label for coupling to a desired target moiety is provided in a kit comprising N-hydroxysulfosuccinimide (sulfo-NHS), a water-soluble carbodiimide (e.g. EDAC) and a label containing an amine or carboxyl moiety, these components being in a dry form suitable for rehydration at pH ranging from 6.0 to 8.0. A typical kit might contain:

Kit 1:
Vial(s) containing powdered NHS, carbodiimide and label, preferably with dessicant pack(s) included in the packaging
Vial(s) containing stop reagent
Column(s) for separation of conjugate from unused label and stop reagent
Bottle(s) containing dry powdered buffer for the loading and elution of conjugate (may be more than one depending on separation method used)

Kit 2:
Vial(s) containing powdered NHS, carbodiimide and label, preferably with dessicant pack(s) included in the packaging
Vial(s) containing stop reagent Kit 3:
Vials containing the powdered NHS, carbodiimide and label, preferably with dessicant pack included in the packaging. Set for multiple labelings.

Production of labeled conjugates—

The dry mix of unreacted label, NHS, and carbodiimide is rehydrated for reaction with the target moiety (typically one member of a specific binding pair) to conjugate the label to the target moiety.

Types of specific binding partners—

The mixing of separate materials in such a manner that they are not reacted until addition of a final "target" component constitutes a composition of matter that is very general and can be applied to phycobiliproteins, PBXL™ dyes, enzymes or literally any carboxyl-containing label. In addition, many organic dyes can be modified to contain a carboxyl using standard organic chemistry. For example, phosgene can be used, in the presence of Friedel-Crafts catalysts, to introduce a carboxyl group to aryl ring structures. March 1985 *J. Advanced Organic Chemistry.*

Suitable target moieties include, but are not limited to: receptors, apatmers, nucleic acids, modified nucleic acids, antibodies (IgG, IgA, IgM, Fc fragment, Fab fragment, F(ab')$_2$ fragment), ligands, pore forming compounds, lectins, peptides, cellular extracts, mixtures of molecules, synthetic antibodies and plastic antibodies and combinatorially produced materials containing free carboxyl groups or free amines that could provide reactive sites.

In one mode of the present invention, a freeze-dried mix of reagents is provided in a small tube, and the user adds the target molecule of interest either directly or after a short preincubation to get the best activation of the proteins, these are incubated for between 30 minors and overnight then a quenching reagent is added. The conjugate can be used as is or purified over a gel permeation column. The freeze-dried mix may be provided in small vials for 1 mg conjugations.

Process Parameters

The sequential addition of reagents and sequestration of each in an inert state gives one the ability to make conjugates in a one step procedure. However, since the reaction does occur simultaneously upon rehydration, certain limitations are imposed on conjugation conditions, such as buffers (particularly pH), offered molar ratio (of various reactants as added to the reaction mixture), and the time of the reaction (both between the two partners (i.e. antibody to enzyme) and between sulfo-NHS and EDAC).

Experiments were done to find an appropriate pH for the optimal labeling. Since EDAC is more reactive at acidic pH's and sulfo-NHS is more reactive at more basic pH's there is a fine pH range (preferably pH 6.8–7.4) for an effective conjugation. Experiments done at pH 6.0, in which EDAC is very reactive and Sulfo-NHS is unreactive, show that no conjugate is formed between APC and streptavidin under these conditions.

The offered molar ratio of protein to binding partner (i.e., label to target) will preferably be experimentally optimized for each set of conjugation partners. For example, preferred ratios for PBXL dyes to SA (1:25) differ from that of APC to SA (1.2:1). Another example is the conjugation of PBXL-3 to rabbit IgG which used an offered ratio of 20 IgG's to 1 PBXL-3 molecule.

The time of the reaction may be optimized. Overnight labeling is more efficient than 2 hour labeling times for APC conjugation to SA. However, 2 hour labeling is more convenient for most researchers.

The time of the reaction between sulfo-NHS and EDAC is important before the addition of binding partner to the rehydrated dye complex. Some of the dyes (labels) are known to rehydrate at different speeds. However, the short lifetimes of the EDAC at near neutral pH requires that the labels rehydrate or at least provide fairly homogeneous solutions promptly to allow even activation and prevent cross-linking of labels to each other.

EXAMPLES

In order to facilitate a more complete understanding of the invention, a number of Examples are provided below. However, the scope of the invention is not limited to specific embodiments disclosed in these Examples, which are for purposes of illustration only.

Example 1

Conjugation of phycoerythrin to streptavidin via 1-ethyl-3-(3-dimethylamino-propyl) carbodiimide (EDAC)/N-hydroysulfosuccinimide (Sulfo-NHS) either directly (Standard Simultaneous Method) or from a freeze-dried reagent (Sequential Freezing Method).

Method: Two procedures for producing conjugates were performed according to the protocols outlined below. In the first procedure (the Standard Simultaneous Method or Standard Method) phycoerythrin (PE) was conjugated with streptavidin (SA) by mixing the two proteins (PE & SA) with EDAC and Sulfo-NHS simultaneously in buffer. The mixture was incubated at room temperature for 2 h to provide the conjugate. In the second procedure (the Sequential Freezing or Invention Method), PE+D-(+)-trehalose, EDAC, and sulfo-NHS solutions of specified content were flash frozen sequentially to prevent interaction of the chemicals, then freeze-dried. After being freeze-dried, the freeze-dried material was resuspended in streptavidin-containing phosphate buffer. The reactants were allowed to react at room temperature for at least 2 h. The resulting conjugate was purified by gel filtration. The concentration and differential binding of conjugates were determined and are reported in the data table following the detailed protocol description below.

Standard Simultaneous Method—B-phycoerythrin (B-PE) was dialyzed against 1 L of 100 mM of sodium phosphate containing 0.05% sodium azide (pH 6.8). This buffer was changed once every hour for 3 h, then the concentration of B-PE was determined by using its extinction coefficient. Streptavidin was then added to an approximately 3 mg/mL B-PE solution at a ratio of 2 to 1 (B-PE/SA). 1 M EDAC was then prepared in the same buffer used above and added into the reaction mixture to obtain a final concentration of 0.05 M EDAC. Then 0.1 M sulfo-NHS solution was prepared using the same buffer as above. Sulfo-NHS was added into the reaction mixture to obtain a final concentration of 0.005 M sulfo-NHS. The reaction was run at room temperature for 2 h. Then the conjugate was purified over SEPHADEX 300 (AMERSHAM PHARMACIA BIOTECH) using 100 mM sodium phosphate, 150 mM NaCl, and 0.05% sodium azide (pH 7.2) as the running buffer.

Sequential Freezing Method—B-PE was dialyzed against 1 L of 100 mM of sodium phosphate containing 0.05% sodium azide (pH 6.8) as above. This buffer was changed once every hour for 3 h. The B-PE concentration was determined by its extinction coefficient. D-(+)-trehalose powder was added into 1 mL of a 3 mg/mL B-PE solution to obtain a final concentration of 0.1 M trehalose. The mixture was vortexed until the powder was dissolved then flash frozen in liquid nitrogen in 1 mL aliquots in microcentrifuge tubes. Then 1 M EDAC and 0.1 M of sulfo-NHS stock solutions were prepared in the same buffer used above. EDAC stock was layered onto the frozen reagent containing the dye in such a volume to obtain a final concentration of 0.05 M EDAC when reconstituted to 1 mL and flash frozen. The sulfo-NHS was added into the above frozen reagents in such a volume to obtain a final concentration of 0.005 M sulfo-NHS in 1 mL final volume and flash frozen. The order of sequential freezing is not critical; however, the rapid freezing of reagents is critical to both maintain the activity of the agent being added, as well as to prevent interaction of the reagents before the rehydration step. The frozen reagents were then freeze-dried overnight. The next day 1 mL of a solution containing SA in distilled water was prepared such that a 2/1 molar ratio of B-PE to SA will be produced on adding it to the tube. The freeze-dried mixture was resuspended in the 1 mL of SA solution and allowed to dissolve. The reaction was run at room temperature for 2 h then stored overnight at 4° C. The conjugate was purified over SEPHADEX 300 (AMERSHAM PHARMACIA BIOTECH) using 100 mM sodium phosphate, 150 mM NaCl, and 0.05% sodium azide (pH 7.2) as the running buffer.

Assay of Differential Binding. A black 96 well MICROTITER plate (DYNEX LABORATORIES) was passively coated with 100 µL per well of 100 µg/mL Biotinated BSA at 37° C. for 4 h. Plates were washed 5 times with single strength PBS buffer (10 mM sodium phosphate (pH 7.0), 150 mM sodium chloride, and 0.05% sodium azide) at 200 µL per well. The plates were then blocked with 100 µL per well of MBB blocking buffer (1.5% BSA, 1% casein, 0.5% gelatin and 0.1% Tween 20 diluted to half strength with PBS at RT for 2 h. After blocking, the plates were washed 5 times with 200 µL per well of 1×PBS. Conjugates were mixed in the indicated concentrations with 100 ng biotin/100 µL or without biotin in 100 mM of sodium phosphate containing 0.05% sodium azide (pH=6.8) buffer and allowed to preincubate for 20 min at room temperature. Then 100 µL of sample (with or without competitive biotin added) was added to the wells of the BSA-biotin precoated plates. These were allowed to react for 1 h at room temperature. Plates were then washed three times with 100 mM sodium phosphate, 150 mM NaCl, 0.05% $NaN_3$ (pH 7.2) with 200 µL per well for each wash. The wet plates were read on a FLUOROLITE 1000 plate reader (DYNEX LABORATORIES) using a 550 nm excitation and 590 nm emission filter set.

Effect of target protein to dye ratio (F/P) on specific binding. In this experiment the fluorescent dye to target protein ratio (F/P) was varied for the freeze-dried samples to see if better conjugates would be produced. To the freeze-dried samples, 0.5 M trehalose was added prior to freeze-drying as a cryoprotective agent in 100 mM sodium phosphate (pH 6:8) buffer. Freeze-drying was carried out in the first experiments for 16 h. The amount of EDAC was 0.05 M and the amount of sulfo-NHS was 0.005 for both the Sequential Freezing Method and Standard Simultaneous Method produced conjugates. The materials were used immediately after preparation. The assay was carried out at room temperature for 2 h then the samples were stored overnight at 4° C. prior to the binding assay.

From the data, the not yet optimized conjugation works better in the Standard Simultaneous Method conjugate but the Sequential Freezing Method seems to work relatively well (±78% differential binding) without further optimization of reagents.

However, the data using an F/P ratio of 2 gave better differential binding than that at 3 for the freeze-dried materials.

| Treatment | Conjugate (µg/mL) | − biotin | + biotin | % Differential Binding |
|---|---|---|---|---|
| Liquid F/P ratio = 3 | 10 | 3506 | 116 | 97 |
| | 5 | 2327 | 105 | 95 |
| | 2.5 | 1100 | 104 | 91 |
| | 0.25 | 466 | 102 | 78 |
| Freeze-Dried F/P ratio = 3 | 10 | 1858 | 403 | 78 |
| | 5 | 730 | 415 | 43 |
| | 2.5 | 427 | 435 | −2 |
| | 0.25 | 405 | 399 | 1 |
| Freeze-Dried F/P ratio = 2 | 10 | nd | nd | nd |
| | 5 | 1688 | 157 | 91 |
| | 2.5 | 649 | 163 | 75 |
| | 0.25 | 176 | 157 | 11 |

Example 2

Effect of longer freeze-drying time on conjugate performance using the Sequential Freezing Method.

In an effort to more closely link performance of the freeze-dried format to liquid materials, a more extensive and exhaustive freeze-drying was carried out in this experiment (64 h versus 16 h) to assure that all liquid was removed from the material. Only two conjugate concentrations were used (10 and 5 μg/mL) and an F/P ratio of 2 was used for all experiments. Otherwise, all conditions were as described in Example 1. No difference was observed between using the dyes for conjugation immediately after freeze-drying or after storage at −20° C. for one week. The differential binding achieved equaled that observed previously for the Standard Simultaneous Method conjugation procedures. It appears that complete drying is critical for the proper performance of these reagents.

| Treatment | Conjugate (μg/mL) | − biotin (cps) | + biotin (cps) | % Differential Binding |
|---|---|---|---|---|
| Freeze-Dried F/P Ratio = 2 Used Immediately | 10 | 2062 | 82 | 96% |
| | 5 | 1085 | 63 | 94% |
| Freeze-Dried F/P Ratio = 2 Stored 1 week | 10 | 1855 | 74 | 96% |
| | 5 | 1173 | 64 | 95% |

Example 3

Effect of pH on conjugates produced from sequential freezing/freeze-dried R-PE activated material.

To determine the optimal range of values for conjugate production from this format, R-PE conjugates to streptavidin were produced as described in Example 2 for B-PE except the 100 mM sodium phosphate buffer was adjusted to different pH values between 6.8 and 7.4 and quenched at 0.1 M lysine after the 2 h reaction at room temperature.

All dyes were offered at a F/P ratio of 2 and reagents used for conjugation immediately after freeze-drying. At the three concentrations of conjugate applied there was little difference in the differential binding observed at these different pH values. At pH 6.8 the best data was achieved but this difference was not substantially better than pH 7.4 and in fact all would probably deliver adequate performance as conjugation reagents.

| pH | Conjugate (μg/mL) | − Biotin (cps) | + Biotin (cps) | % Differential Binding |
|---|---|---|---|---|
| 6.8 | 10 | 1975 | 75 | 96 |
| | 5 | 1159 | 73 | 94 |
| | 2.5 | 513 | 74 | 86 |
| 7.0 | 10 | 1840 | 74 | 96 |
| | 5 | 1083 | 70 | 94 |
| | 2.5 | 383 | 77 | 80 |
| 7.2 | 10 | 1755 | 76 | 96 |
| | 5 | 555 | 68 | 88 |
| | 2.5 | 285 | 70 | 75 |
| 7.4 | 10 | 1633 | 72 | 96 |
| | 5 | 736 | 64 | 91 |
| | 2.5 | 254 | 68 | 73 |

Example 4

Functional Stability of Freeze-dried Reagents on Storage at −20° C.

The need for stable product is obvious for this invention. A short-term study to determine if the products rapidly degraded was performed using B-PE made and freeze-dried as described in Example 3 except that 0.1 M trehalose was used in the freezing medium. Reactions were performed at pH 6.8 and not quenched. At least up to three weeks of storage seemed to have little or even a beneficial effect on the conjugates produced with these reagents.

| Storage Time (weeks) | Conjugate (μg/mL) | − Biotin (cps) | + Biotin (cps) | % Differential Binding |
|---|---|---|---|---|
| 0 | 10 | 2023 | 209 | 90 |
| | 5 | 1206 | 185 | 85 |
| 1 | 10 | 902 | 77 | 91 |
| | 5 | 264 | 72 | 73 |
| 2 | 10 | 2920 | 63 | 98 |
| | 5 | 1579 | 61 | 96 |
| | 2.5 | 474 | 58 | 88 |
| 3 | 10 | 2360 | 57 | 98 |
| | 5 | 990 | 57 | 94 |
| | 2.5 | 394 | 56 | 86 |

Example 5

Conjugation of chemically stablized phycobilisomes (PBXL-3; MARTEK BIOSCIENCES) to streptavidin using the sulro-NHS/EDAC/D-(+)-trehalose Sequential Freezing Method.

The Sequential Freezing Method (Invention Method) was compared to the Standard Simultaneous Method for making PBXL-3 labeled streptavidin conjugates. In the Standard Simultaneous Method, PBXL-3 was combined with streptavidin (SA), EDAC and Sulfo-NHS in buffer and reacted simultaneously in a manner analogous to literature methods. The mixture was incubated at room temperature for 2 h. In the Sequential Freezing Method, the following reagents were sequentially freeze-dried: PBXL-3 in 100 mM sodium phosphate plus D-(+)- Trehalose, 1 M EDAC and 0.1 M sulfo-NHS in defined volumes. The frozen materials were freeze-dried overnight, then the dried powder was resuspended in streptavidin-containing very low concentration phosphate buffer. This was allowed to react for 2 h at room temperature. The conjugates were then purified by gel filtration over SEPHAROSE 6B. The differential binding of conjugates was determined and compared for performance of the conjugation formats.

Protocol:

Standard Simultaneous Method—PBXL-3 was dialyzed again 1 L of 100 mM of sodium phosphate (pH 7.4) with buffer changes once an hour for 3h. The concentration of PBXL-3 was determined by its absorbance at 620 nm (5 Au/mg PBXL3). Streptavidin was added to the PBXL-3 solution at an F/P ratio of 0.4 or 25 SA per PBXL-3 complex. A 1 M stock of EDAC was prepared in the same buffer used above and added into the reaction mixture to obtain a final concentration of 0.05 M. A 0.1 M of Sulfo-NHS solution was prepared using the same buffer as above and added into the reaction mixture to obtain a final concentration of 0.005 M. This was reacted at room temperature for 2h. The conjugate was purified over SEPHAROSE CL6B (AMERSHAM PHARMAC1A BIOTECH) using 100 mM sodium phosphate, 150 mM NaCl, and 0.05% sodium azide (pH 7.2) as the running buffer.

Sequential Freezing Method—PBXL-3 was dialyzed against 1 L of 100 mM of sodium phosphate (pH 7.4) and the buffer was changed once every hour for 3 h. The concentration of PBXL-3 was determined by its absorbance at 620 nm (5 Au/]

mg protein). This was mixed (by vortexing) with D-(+)-Trehalose powder to a final concentration of 0.5 M then aliquoted into microcentrifuge tubes and flash frozen in liquid nitrogen or on a methano/dry ice bath. A 1 M EDAC stock solution was made in the same buffer used above and added, in such a volume to deliver (on mixing of all reagents) a final concentration of 0.05 M, on top of the frozen material while still under liquid nitrogen temperatures to achieve nearly instant freezing of the added materials. A 0.1 M of sulfo-NHS solution was made using the same buffer as above and added, in such a volume to deliver on mixing of all reagents a final concentration of 0.005 M, on top of the previously frozen reagents still under liquid nitrogen temperatures to achieve nearly instant freezing of the added materials. This was freeze-dried overnight. A solution containing SA in various molar ratios was prepared using the same buffer as above. This SA solution was used to resuspend the freeze-dried mixture to the volume of solution before the freeze-drying step (to keep all reagents at defined concentrations). The resuspended reagents and SA were reacted together at room temperature for 2 h. The resulting conjugate as purified over SEPHAROSE CL6B (AMERSHAM PHARMACIA) using 100 mM sodium phosphate, 150 mM NaCl and 0.05% sodium azide (pH 7.2) as the running buffer.

Differential binding assay. A black 96 well MICROTITER plate (DYNEX LABORATORIES) was passively coated with 100 µL per well of 100 µg/mL Biotinylated BSA at 37° C. for 4 h. Plates were washed five times with 1×PBS and blocked with MBB blocking buffer as previously described. Plates were washed five times with 200 µL per well of 1×PBS. Conjugate with or without 100 ng biotin/100 µL were mixed together as indicated in the table in Assay Buffer and preincubated for 20 min before adding into wells. Preincubated materials were added at 100 µL/well and allowed to react at room temperature for 1 h. Plates were washed three times with 200 µL per well 100 mM sodium phosphate (pH 7.2), 150 mM NaCl, 0.05% NaN₃ buffer. Plates were then read on the FLUOROLITE 1000 (DYNEX LABORATORIES) using a 590 nm filter for excitation and a 660 nm filter for emission, the voltage was set at 7.7V.

| Treatment* | Conjugate µg/mL | − biotin (cps) | + biotin (cps) | % Differential Binding |
|---|---|---|---|---|
| Simultaneous | 50 | over | 30 | nd |
| PBXL-3/SA ratio = 25 | 25 | 3056 | 15 | 100 |
| Liquid Reagents | 12.5 | 1594 | 11 | 99 |
|  | 6.25 | 642 | 8 | 99 |
| Sequential | 36 | 903 | 17 | 98 |
| PBXL-3/SA ratio = 25 | 18 | 115 | 14 | 88 |
| Freeze-Dried Reagents | 9 | 10 | 10 | 0 |
|  | 4.5 | 8 | 8 | 0 |

*Simultaneous = Standard Simultaneous Method; Sequential = Sequential Freezing Method or Invention Method

Example 6

Comparison of Sequential Freezing Method to the Standard Simultaneous Method for EDAC/sulfo-NHS cross-linking and to another standard cross-linking method, SMCC/SATA.

Another set of experiments was done comparing conjugates made by the two sulfo-NHS/EDAC methods (Sequential Freezing and Standard Simultaneous Methods) as described in Example 5 and a standard SMCC/SATA conjugation method. Similar performance was provided by all of these methods.

| Conj. µg/mL | Simultaneous Sulfo-NHS/EDAC | | Sequential Sulfo-NHS/EDAC | | SMCC/SATA | |
|---|---|---|---|---|---|---|
|  | − Biotin/ + Biotin | % Δ Binding | − Biotin/ + Biotin | % Δ Binding | − Biotin/ + Biotin | % Δ Binding |
| 50 | 729/4 | 99% | 280/2 | 99% | 451/6 | 99% |
| 25 | 516/3 | 99% | 42/2 | 95% | 194/4 | 99% |

*Simultaneous = Standard Simultaneous Method; Sequential = Sequential Freezing Method or Invention Method

Example 7

Conjugation of allophycoyanin (APC) to streptavidin via the sulfo-NHS/EDAC Sequential Freezing Method (Invention) compared to Standard Simultaneous Method.

Method: The Invention Method was compared to a Standard Simultaneous Method for the ability to produce functional APC labeled streptavidin conjugates. In the Standard Simultaneous Method, APC was combined with streptavidin (SA), EDAC and sulfo-NHS simultaneously. Then the mixture was incubated at room temperature for 2 h to form a conjugate and the conjugate purified by gel permeation. In the Sequential Freezing Method, APC was mixed with D-(+)-trehalose and frozen. A specific amount of EDAC solution was then layered on top of the frozen dye and flash frozen, then a solution of sulfo-NHS was layered on top of the frozen reagents and flash frozen. The unmixed (due to flash freezing), frozen reagents were freeze-dried overnight. The dry reagents were resuspended in streptavidin-containing low phosphate buffer and reacted at room temperature at least 2 h. The resulting conjugates were purified by gel filtration. The concentration and differential binding of conjugates were determined and compared for their ability to bind biotin specifically.

Protocol:

Standard Simultaneous Method—APC was dialyzed against 1 L of 100 mM of sodium phosphate containing 0.05% sodium azide (pH 7.2) changing the buffer once every hour for 3 h. APC concentration was determined using its extinction coefficient. Streptavidin was added to a 3-5 mg/mL APC solution at a ratio 1.2 to 1 of F/P (fluor to target protein). A 1 M EDAC solution was prepared in the same buffer used above then added to the reaction mixture to obtain a final concentration of 0.05 M EDAC. A 0.1 M stock solution of sulfo-NHS was made in the same buffer as above then added into the reaction mixture to obtain a final concentration of 0.005 M sulfo-NHS. The reaction mixture was incubated at room temperature at least 2 h. The resulting conjugate was purified over a SEPHADEX 300 column (AMERSHAM PHARMACIA) using 100 mM sodium phosphate, 150 mM NaCl, 0.05% sodium azide (pH 7.2) as the running buffer.

Sequential Freezing Method—APC was dialyzed and quantitated as above. D-(+)-Trehalose powder was added to a 3–5 mg/mL APC solution to obtain a final concentration of 0.5 M trehalose. The mixture was vortexed mixed until the powder was dissolved. This was aliquoted and flash frozen in liquid nitrogen or a dry ice/methanol bath. Then 1 M of EDAC and 0.1 M sulfo-NHS stocks were prepared as described above. Aliquots of EDAC solution were layered on top of the frozen pigment solution, in such a volume to deliver a final concentration of 0.05 M on resuspension, while the tubes were still in the freezing solution to provide flash freezing of the EDAC addition. The sulfo-NHS stock was added, in such a volume to obtain a final concentration of 0.005 M, on top of the reagents already frozen in the tube while still in the freezing solution to provide rapid freezing of the sulfo-NHS reagent. Frozen reagents were then freeze-dried overnight. An aqueous SA solution that will deliver a F/P ratio of 1.2/1 was made then used to resuspend the freeze-dried reagents to 1 mL. These; reacted at room temperature for 2 h then were stored overnight at 4° C. The resulting conjugate was purified as described above.
Differential binding assay—Done as previously described for PBXL-3 using the 590 nm excitation and 660 nm emission filter set.

The Sequential Freezing Method for NHS/EDAC mediated cross-linking described in this invention compares very well to the simultaneous mixing method in giving consistently high differential binding with the APC labeled streptavidin to BSA biotin plates in the presence or absence of competing biotin. Trehalose does not seem to be necessary for storage of up to one week at −20° C.

| Treatment* | Conjugate (µg/mL) | − biotin (cps) | + biotin (cps) | % Differential Binding |
|---|---|---|---|---|
| Simultaneous | 10 | 4013 | 16 | 100 |
| Liquid | 5 | 3894 | 11 | 100 |
| Simultaneous | 10 | 3638 | 14 | 100 |
| Liquid | 5 | 2712 | 10 | 100 |
| Sequential | 10 | 2198 | 11 | 99.5 |
| Freeze-dried | 5 | 2039 | 10 | 99.5 |
| No trehalose | 2.5 | 1273 | 10 | 99.2 |
| | 0.25 | 114 | 9 | 92 |
| Sequential | 10 | 2349 | 11 | 99.5 |
| Freeze-dried | 5 | 2146 | 9 | 99.6 |
| 0.1 M trehalose | 2.5 | 998 | 10 | 99 |
| | 0.25 | 42 | 9 | 78 |
| Sequential | 10 | 3182 | 19 | 99.4 |
| Freeze-dried | 5 | 2842 | 13 | 99.5 |
| No trehalose | 2.5 | 2225 | 13 | 99.4 |
| 1 week storage | 0.25 | 244 | 11 | 99.5 |

*Simultaneous = Standard Simultaneous Method; Sequential = Sequential Freezing Method or Invention Method Example 8

Conjugation of PBX-3 (MARTEK BIOSCIENCES) to Goat anti-Rabbit IgG using via the sulfo-NHS/EDAC Sequential Freezing Method (Invention).

Method and Protocol: In this experiment PBXL-3 was dialyzed and quantitated as above. D-(+)-Trehalose powder was added to a 3 mg/mL PBXL-3 solution to obtain a final concentration of 0.5 M trehalose. The mixture was vortexed mixed until the powder was dissolved. This was aliquoted and flash frozen in liquid nitrogen bath. Then 1 M of EDAC and 0.1 M sulfo-NHS stocks were prepared as described above. Aliquots of EDAC were layered on top of the frozen pigment solution, in such a volume to deliver a final concentration of 0.05 M on resuspension (1 mL), while the tubes were still in the freezing solution to provide flash freezing of the EDAC addition. The sulfo-NHS stock was added, in such a volume to obtain a final concentration of 0.005 M, on top of the reagents already frozen in the tube while still in the freezing solution to provide rapid freezing of the sulfo-NHS reagent. Frozen reagents were then freeze-dried overnight. An aqueous Goat anti-Rabbit IgG solution that will offer a F/P ratio of 2/1 was made then used to resuspend the freeze-dried reagents to 1 mL. These reacted at room temperature for 2 h then were stored overnight at 4° C. The resulting conjugate was purified as described above.
Differential binding assay—Done as previously described for PBXL-3 using the 590 nm excitation and 660 nm emission filter set.

This sequential method although not optimized in this example, illustrates that commercially available antibodies can be attached to PBXL dyes. These conjugates then could be used in function binding assays.

| Treatment* | Conjugate µg/mL | − Rabbit 1 gG (cps) | + Rabbit 1 gG (cps) | % Differential Binding |
|---|---|---|---|---|
| Sequential | 50.00 | 170 | 38 | 77.6 |
| | 25.00 | 70 | 28 | 60.0 |
| | 12.50 | 58 | 23 | 60.3 |
| | 6.25 | 42 | 22 | 47.6 |

Sequential = Sequential Freezing Method or Invention Method

Example 9

Determination of the optimal time for addition of target protein (streptavidin) to resuspended freeze-dried reagents using the sulf-NHS/EDAC chemistry formatted as the Sequential Freezing Method.

Figure 2:
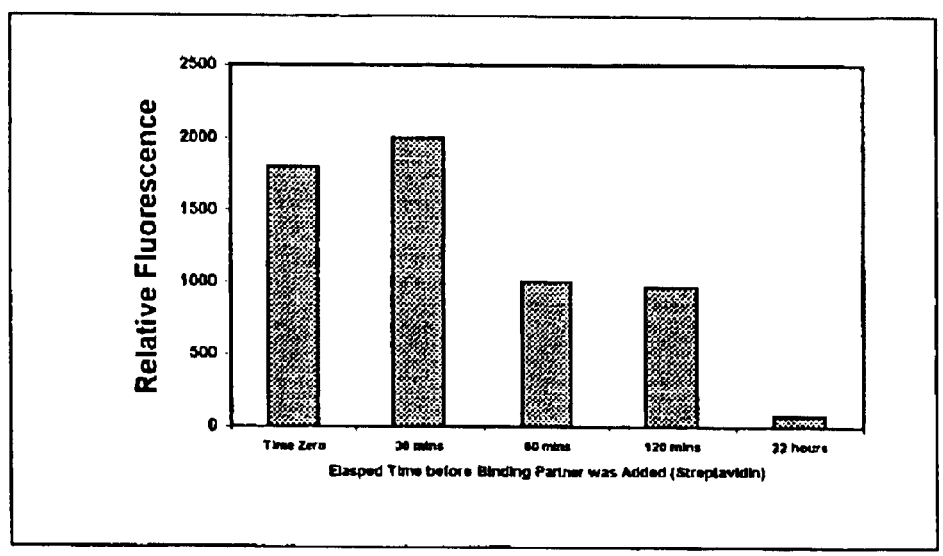
FIG. 2 is a bar graph showing an example of a time course used to optimize the time for addition of the conjugal partner.

The data in FIG. 2 illustrate an example of a time course used to determine when is the optimal time to add the conjugation partner in the Sequential Freezing Method. An essential question for the ease of use of this method was to determine if it could be made as a one step (add the protein in solution and you are done) versus rehydrate and add at some optimal time later. This was done mostly to see how much better the conjugates could be produced since it was thought that unrestricted cross-linking of the wrong reagents might occur if you did not first activate the label before adding the binding partner.

Differential binding assay—The binding assay was carried out as previously described for PBXL-3 using the 590 nm excitation and 660 nm emission filter set. FIG. 2 illustrates the importance of adding the binding partner within a half hour of rehydrating the sequentially frozen sample. Conjugation efficiency is greatly affected by having the chemical reactants and the PBXL-3 in solution for sustained lengths of time prior to addition of the binding partner. Interestingly, there is not a large increase in functional effectiveness between adding the binding partner after 30 min (when the dye would be fully activated) and adding the binding partner immediately. This is unexpected and provides a very simple format for the Sequential Freezing Method (rehydrate with an aqueous suspension of the target protein, incubate, purify and use).

Because solution phase chemical reactants become ineffective the longer one waits prior to addition of binding partner, formats that store liquid materials would not be suitable for this type of reaction. After twenty-four hours, the reactive groups are no longer functional. This data illustrates the utility for spatial or temporal separation between the NHS, EDAC and PBXL-3 provided by the Sequential Freezing Method in providing a simple and rapid method for making useful conjugates.

Example 10

Stability of PBX-3 labeled streptavidin produced using the Sequential Freezing Method.

Figure 3:
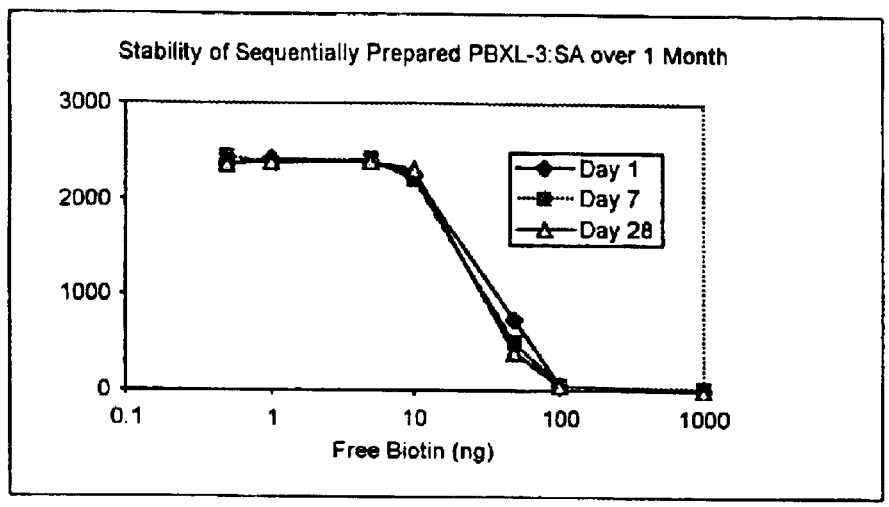
FIG. 3 shows biotin dose response curves generated with activated dyes at three time points.

The stability of a PBXL-3 labeled streptavidin conjugate was evaluated at several time points to determine if adequate stability was present with labeled proteins produced with the Sequential Freezing Method. The binding assay was done as previously described except that a biotin dose response curve was generated at each time point to better evaluate the stability of these conjugates. FIG. 3 shows three biotin dose response curves corresponding to three samples made from one run of the Sequential Freezing Method that were rehydrated over the course of one month (1 day, 7 days, 29 days) and conjugated to the same lot of streptavidin on the day of rehydration. The three virtually over lapping free biotin dose response curves indicate that the labeling of the PBXL-3 to streptavidin is fairly consistent throughout one month's storage time of the freeze-dried reagents described by this invention.

What is claimed is:

1. A single vessel containing N-hydroxysuccinimide (NHS), a water-soluble carbodiimide and a label containing an amine or a carboxyl moiety, these components being in a single vessel in dry form suitable for rehydration at pH about 7.

2. A single vessel containing a label derivatized with one functionality of a heterofunctional reagent and means for activating the unreacted functionality of the heterofunctional reagent or its reaction partner, these components being in a single vessel in dry form suitable for rehydration.

3. A method of conjugating label to target moiety, comprising:
    a. derivatizing a label containing primary or secondary amines with a heterobifunctional reagent having a maleimide functionality;
    b. placing maleimide derivatized label in a container with a reductant in dry form;
    c. hydrating label and reductant; and
    d. removing reductant in the presence of a target moiety, whereby the target moiety is conjugated to the label.

4. A method for conjugating label to target moiety comprising:
    a. placing a label, NHS, and a carbodiimide in a container such that the three components are sequestered from reaction with each other;
    b. storing the components in dry form; and
    c. hydrating the components to initiate reaction between them,
        wherein a target is added at the time the components are hydrated and the target is subsequently conjugated to the label.

5. A method for conjugating label to target moiety comprising:
    a. placing a label, NHS, and a carbodiimide in a container such that the three components are sequestered from reaction with each other;
    b. storing the components in dry form; and
    c. hydrating the components to initiate reaction between them,
        wherein a target is added subsequent to hydrating the components and the target is conjugated to the label.

* * * * *